United States Patent
Kannusamy et al.

(10) Patent No.: US 12,285,411 B2
(45) Date of Patent: Apr. 29, 2025

(54) PHARMACEUTICAL COMPOSITION COMPRISING ELUXADOLINE, PROCESS OF PREPARATION AND USE THEREOF

(71) Applicants: Saravanan Kannusamy, Hyderabad (IN); Venkata Vijaya Narasimha Kishan Jayanthy, Hyderabad (IN); Aman Taqiuddin Mohammed, Hyderabad (IN); Raja Rao Chinta, Hyderabad (IN); Sivakumaran Meenakshisunderam, Hyderabad (IN)

(72) Inventors: Saravanan Kannusamy, Hyderabad (IN); Venkata Vijaya Narasimha Kishan Jayanthy, Hyderabad (IN); Aman Taqiuddin Mohammed, Hyderabad (IN); Raja Rao Chinta, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 793 days.

(21) Appl. No.: 17/014,675

(22) Filed: Sep. 8, 2020

(65) Prior Publication Data
US 2021/0106563 A1    Apr. 15, 2021

(30) Foreign Application Priority Data
Sep. 10, 2019    (IN) .............................. 201941036255

(51) Int. Cl.
*A61K 31/4164* (2006.01)
*A61K 9/00* (2006.01)
*A61K 9/20* (2006.01)
*A61K 9/28* (2006.01)

(52) U.S. Cl.
CPC ........ *A61K 31/4164* (2013.01); *A61K 9/0053* (2013.01); *A61K 9/2018* (2013.01); *A61K 9/2027* (2013.01); *A61K 9/2054* (2013.01); *A61K 9/2095* (2013.01); *A61K 9/2813* (2013.01); *A61K 9/282* (2013.01)

(58) Field of Classification Search
CPC .................................................. A61K 31/4164
See application file for complete search history.

(56) References Cited

U.S. PATENT DOCUMENTS 9,675,587 B2 *   6/2017   Allergan ................ A61K 47/26

OTHER PUBLICATIONS

Drugs.com. "Viberzi; Generic Name eluxadoline". Published Mar. 22, 2016. Accessed via WayBackMachine (Internet Archive) on Feb. 9, 2023. Available from: < Viberzi—FDA prescribing information, side effects and uses (archive.org) > . (Year: 2016).*
DrugBank Online. "Hypromellose". Published Sep. 11, 2017. Accessed Feb. 9, 2023. Available from: < https://go.drugbank.com/salts/DBSALT001498 > . (Year: 2017).*
SPI Pharma. Published May 20, 2015. "Lubripharm SSF". Accessed Feb. 9, 2023. Available from: < https://www.spipharma.com/en/products/functional-excipients/lubripharm-ssf/ > . (Year: 2015).*
Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*

* cited by examiner

*Primary Examiner* — John S Kenyon
(74) *Attorney, Agent, or Firm* — Jay R. Akhave; PatentScience LLC

(57) ABSTRACT

The present invention relates to oral pharmaceutical compositions comprising eluxadoline or a prodrug or a pharmaceutically acceptable salt thereof, and one or more pharmaceutically acceptable excipients, and process for the preparation thereof and administration of such compositions for irritable bowel syndrome (IBS-D).

4 Claims, No Drawings

PHARMACEUTICAL COMPOSITION COMPRISING ELUXADOLINE, PROCESS OF PREPARATION AND USE THEREOF

CROSS REFERENCE TO RELATED APPLICATIONS

This application claims priority from an Indian Patent Application IN 201941036255 filed on Sep. 10, 2019.

FIELD OF THE INVENTION

The present disclosure relates to oral pharmaceutical compositions comprising an opioid receptor modulator, process for the preparation thereof and administration of such compositions for opioid receptor related disorders including, for example, pain and gastrointestinal disorders such as diarrheic syndromes, motility disorders including post-operative ileus and constipation, and visceral pain including post-operative pain, irritable bowel syndrome and inflammatory bowel disorders.

The present disclosure relates to oral pharmaceutical compositions comprising eluxadoline or a pharmaceutically acceptable salt thereof or a prodrug thereof, process for the preparation thereof and administration of such compositions for irritable bowel syndrome (IBS-D).

BACKGROUND OF THE INVENTION

The opioid receptors were identified in the mid-1970's, and were quickly categorized into three sub-sets of receptors (mu, delta and kappa). More recently the original three types of receptors have been further divided into sub-types. Also known is that the family of opioid receptors are members of the G-protein coupled receptor (GPCR) super-family More physiologically pertinent are the well established facts that opioid receptors are found throughout the central and peripheral nervous system of many mammalian species, including humans, and that modulation of the respective receptors can elicit numerous, albeit different, biological effects, both desirable and undesirable (D. S. Fries, "Analgesics", in Principles of Medicinal Chemistry, 4th ed.; W. O. Foye, T. L. Lemke, and D. A. Williams, Eds.; Williams and Wilkins: Baltimore, Md., 1995; pp. 247-269; J. V. Aldrich, "Analgesics", Burger's Medicinal Chemistry and Drug Discovery, 5. sup.th Edition, Volume 3: Therapeutic Agents, John Wiley & Sons, Inc., 1996, pp. 321-441). In the most current literature, the likelihood of heterodimerization of the sub-classes of opioid receptors has been reported, with respective physiological responses yet undetermined (Pierre J. M. Riviere and Jean-Louis Junien, "Opioid receptors: Targets for new gastrointestinal drug development", Drug Development 2000, pp. 203-238).

5-({[2-Amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid is an opioid receptor modulator (mu receptor agonist and delta receptor antagonist) and may be useful for treating irritable bowel syndrome, pain or other opioid receptor disorders and methods of making this molecule are disclosed in U.S. Pat. No. 7,741,356. Example 9 of U.S. Pat. No. 7,741,356 makes the hydrochloride salt of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. Further, the applicants of U.S. Pat. Nos. 8,691,860, 9,115,091, 9,364,489 & 9,789,125 have discovered a process of making the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid [Hereafter referred as Eluxadoline] and two novel crystals of this zwitterion (a Form α and a Form β crystals, compositions and method of treating a mammal suffering from irritable bowel syndrome comprising administering to said mammal an effective amount of Form α and Form β.

VIBERZI is an FDA approved drug product comprising of eluxadoline, a mu-opioid receptor agonist has a molecular weight of 569.65 and a molecular formula of $C_{32}H_{35}N_5O_5$. The chemical structure of eluxadoline is:

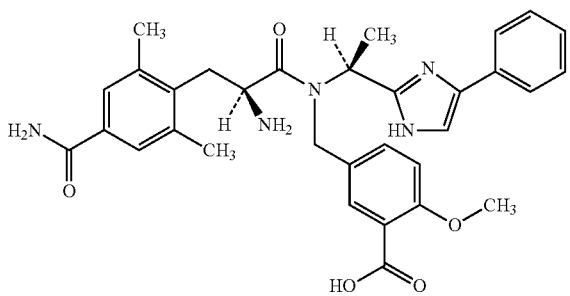 [SMILES: COc1ccc(CN(C(=O)[C@@H](N)Cc2c(C)cc(C(N)=O)cc2C)[C@@H](C)c2nc(-c3ccccc3)c[nH]2)cc1C(=O)O]

VIBERZI is available in the USA as 75 mg and 100 mg tablets for oral administration. In addition to the active ingredient, eluxadoline, each tablet contains the following inactive ingredients: silicified microcrystalline cellulose, colloidal silica, crospovidone, mannitol, magnesium stearate, and Opadry II (partially hydrolyzed polyvinyl alcohol, titanium dioxide, polyethylene glycol, talc, iron oxide yellow, and iron oxide red).

U.S. Pat. Nos. 9,675,587 and 10,188,632 of Allergan Holdings Unlimited company, disclose oral dosage formulations containing eluxadoline, processes for the preparation thereof and administration of these formulations. These are an abuse deterrent, mono-phasic pharmaceutical compositions suitable for single dose administration for treating a condition mediated by an opioid receptor consisting essentially of about 20 mg/dose to about 200 mg/dose of eluxadoline, from about 60-80% by weight of silicified microcrystalline cellulose, from about 0.55-0.95% by weight of colloidal silica, from about 5-15% by weight of mannitol, from about 3-7% by weight of crospovidone, from about 0.55-0.95% by weight of magnesium stearate, and a water-soluble, pH-independent film coating. The abuse deterrent oral pharmaceutical formulations of eluxadoline with improved stability and shelf life and unique physico-chemical features that deter or limit abuse of the active ingredient or diversion of the oral formulations. The abuse deterrent oral pharmaceutical formulations of eluxadoline were assessed by the extraction of the oral formulations with water or saline at 25° C. for up to 12 hours which produces a concentration of eluxadoline of less than or approximately 4 mg/ml.

It is desirable to provide oral pharmaceutical compositions of eluxadoline which are easy to make, commercially viable and provide adequate patient compliance for the treatment of opioid receptor related disorders like IBS-D.

SUMMARY OF INVENTION

An aspect of the present invention relates to oral pharmaceutical compositions comprising an opioid receptor modulator, process for the preparation thereof and administration of such compositions for opioid receptor related disorders including, for example, pain and gastrointestinal disorders such as diarrheic syndromes, motility disorders including post-operative ileus and constipation, and visceral pain including post-operative pain, irritable bowel syndrome and inflammatory bowel disorders.

An aspect of the present invention relates to oral pharmaceutical compositions comprising eluxadoline or a pharmaceutically acceptable salt thereof or a prodrug thereof, process for the preparation thereof and administration of such compositions for irritable bowel syndrome (IBS-D). Specifically, the present invention relates to tablets comprising eluxadoline and excipients selected from silicified microcrystalline cellulose, mannitol, hypromellose, crospovidone, colloidal silicon dioxide, sodium stearyl fumarate and optionally, coating agents An aspect of the present invention relates to an oral pharmaceutical composition comprising:
   (a) Eluxadoline or a pharmaceutically acceptable salt thereof or a prodrug thereof, in an amount from about 5 to 20% by weight of the total composition;
   (b) One or more diluents selected from silicified microcrystalline cellulose and mannitol in an amount from about 10% to about 90% by weight of the total composition;
   (c) Hypromellose in an amount from about 1% to about 10% by weight of the total composition;
   (d) Crospovidone in an amount from 0% to about 2.5% by weight of the total composition;
   (e) Colloidal silicon dioxide in an amount from about 0.5% to about 5% by weight of the total composition;
   (f) Sodium stearyl fumarate in an amount from about 1.25% to about 5% by weight of the total composition; and
   (g) Optionally coating agent.

An aspect of the present invention relates to process of making an oral pharmaceutical composition comprising Eluxadoline or a pharmaceutically acceptable salt thereof or a prodrug thereof prepared by: i) blending eluxadoline or a pharmaceutically acceptable salt thereof or a prodrug thereof, with the pharmaceutically acceptable inert excipients: silicified microcrystalline cellulose, mannitol, hypromellose, colloidal silica and crospovidone; ii) lubricating the above blend with the addition of sodium stearyl fumarate; iii) compressing the dry blend into suitably sized tablets and optionally a film coating, or filling the dry blend into capsules.

DETAILED DESCRIPTION OF THE INVENTION

As used herein, "a" or "an" means one or more unless otherwise specified.

Open terms such as "include," "including," "contain," "containing" and the like mean "comprising".

The term "treatment" or "treating" refers to administering a therapy in an amount, manner, or mode effective to improve a condition, symptom, or parameter associated with a disorder.

The term "Opioid receptor related disorders" includes but not limited to, for example, pain and gastrointestinal disorders such as diarrheic syndromes, motility disorders including post-operative ileus and constipation, and visceral pain including post-operative pain, irritable bowel syndrome and inflammatory bowel disorders.

The term "Irritable bowel syndrome" (IBS) refers to a group of symptoms that occur together, including repeated pain in your abdomen and changes in your bowel movements, which may be diarrhea, constipation, or both. With IBS, you have these symptoms without any visible signs of damage or disease in your digestive tract.

The term "Administering" or "administration" means providing a drug to a patient in a manner that is pharmacologically useful.

The term "Patient" or "subject" means an animal, preferably a mammal, more preferably human, in need of therapeutic intervention.

The term "or" can be conjunctive or disjunctive.

The term "% by weight" is based on the weight of the total composition.

The term "excipient" means a pharmacologically inactive component such as a solvent, diluent, disintegrant, carrier, or the like. The excipients that are useful in preparing a pharmaceutical composition are generally safe, inert, non-toxic and are acceptable for human use. Reference to an excipient includes both one and more than one such excipient.

The term "Oral pharmaceutical composition" or "composition" or "formulation" or "dosage form" or "medicinal preparation" as used herein synonymously (or interchangeably) include any oral solid dosage forms such as granules, multi-unit particulate systems (MUPS), pellets, spheres, tablets, capsules, mini-tablets, layered tablets (e.g. bilayer or trilayer), inlaid tablets, tablet in tablet, beads, particles, pellets presented in a sachet, capsule or tablet capsules such as soft and hard gelatin; lozenges or sachets; granulates, microparticles, multiparticulates, powder and the like, and liquid dosage forms such as solutions, suspensions, emulsions, colloids and the like, meant for oral administration.

The term "pharmaceutically acceptable salt" refers to any non-toxic "pharmaceutically acceptable salts" (Ref. International J. Pharm., 1986, 33, 201-217; J. Pharm. Sci., 1997 (January), 66, 1, 1). Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The term "prodrug" means an ester or carbonate, or any other form which can get converted at least substantially into eluxadoline particularly upon in-vivo administration.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

In certain embodiments, the present invention provides oral pharmaceutical compositions comprising eluxadoline or a pharmaceutically acceptable salt thereof or a prodrug thereof along with one or more pharmaceutically acceptable excipients, process for the preparation thereof and the administration of such compositions for the treatment of opioid receptor related disorders like irritable bowel syndrome (IBS-D).

In certain embodiments, the present invention provides oral pharmaceutical compositions comprising a crystalline or amorphous eluxadoline of formula I.

Formula I

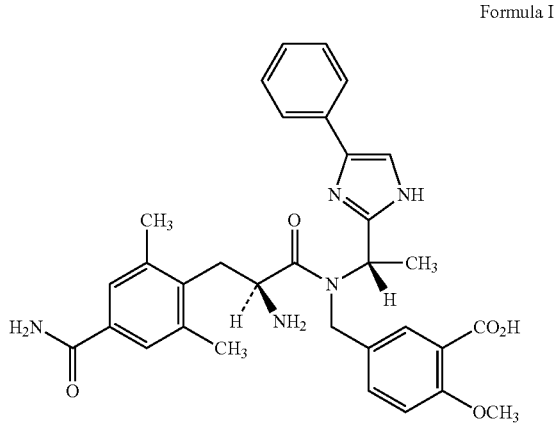 [SMILES: COc1ccc(CN(C(=O)[C@@H](N)Cc2c(C)cc(C(N)=O)cc2C)[C@@H](C)c2nc(-c3ccccc3)c[nH]2)cc1C(=O)O]

The compound of Formula (I) of the present invention also includes pharmaceutically acceptable enantiomers, diastereomers, racemates, zwitterions and salts thereof.

The compositions of the present invention may be provided in any pharmaceutically acceptable solid dosage form(s). Preferably, the solid dosage form includes, for example, solid preparation such as tablets, pills, granules, capsules, powders and others. In embodiments, the solid dosage form is an oral tablet or capsule formulation. In an embodiment, the solid dosage form is an oral tablet which may contain one or more pharmaceutically acceptable excipients selected from diluents, binders, disintegrants, glidants, lubricants, coating agents, colorants and others.

In certain embodiments, the present invention provides a pharmaceutical composition comprising:
  (a) Eluxadoline or pharmaceutically acceptable salt thereof or a prodrug thereof, in an amount from about 5 to 20% by weight of the total composition;
  (b) Diluents in an amount from about 10% to about 90% by weight of the total composition;
  (c) Binders in an amount from about 1% to about 10% by weight of the total composition;
  (d) Disintegrants in an amount from 0% to about 2.5% by weight of the total composition;
  (e) Lubricants in an amount from about 1.25% to about 5% by weight of the total composition;
  (f) Glidants in an amount from about 0.5% to about 5% by weight of the total composition; and
  (g) Optionally coating agent(s).

The composition of the present invention is oral tablets which may contain excipients/additives generally used in pharmaceutical oral tablets. Examples of the excipients include diluents, binders, disintegrants, glidants, lubricants, coating agents, colorants and others.

Examples of the diluents or fillers also include cellulose derivatives, such as microcrystalline cellulose or wood cellulose, lactose, sucrose, starch, pregelatinized starch, dextrose, mannitol, fructose, xylitol, sorbitol, corn starch, modified corn starch, inorganic salts such as calcium carbonate, calcium phosphate, dicalcium phosphate, calcium sulfate, dextrin/dextrates, maltodextrin, and compressible sugars. In certain embodiments, the composition of the present invention includes two diluents, a combination of microcrystalline cellulose in the range of about 40% to about 85% by weight of the total composition and mannitol in the range of about 5% to about 20% by weight of the total composition. In one of the particular embodiments, the composition of the present invention comprises two diluents, preferably, microcrystalline cellulose from about 60% to about 70% by weight of the total composition and mannitol from about 8% to about 12% by weight of the total composition.

Examples of disintegrants suitable for use herein include croscarmellose sodium, crospovidone, starch, potato starch, pregelatinized starch, corn starch, sodium starch glycolate, low substituted hydroxypropyl cellulose and other known disintegrants. In certain embodiments of the present invention the composition includes crospovidone, a disintegrant in the amount of 0% to about 2.5% by weight of the total composition. In one of the particular embodiments, the composition of the present invention comprises crospovidone, a disintegrant in the amount of about 2.5% by weight of the total composition.

Examples of binders for use in accordance with the present invention include but are not limited to cellulose and its derivatives including, hydroxypropylmethylcellulose (Hypromellose), hydroxypropylcellulose, cellulose, cellulose acetate, ethylcellulose, methylcellouse, and hydroxyethylcellulose; starch and its derivatives; pregelatinized starch, starch, hydrocolloids; sugar; polyvinyl pyrrolidone, copovidone, methacrylic acid copolymers and combinations thereof, and the like. In certain embodiments of the present invention the composition includes hydroxypropyl methylcellulose, a binder in the amount of about 1% to about 10% by weight of the total composition. In one of the particular embodiments, the composition of the present invention comprises hydroxypropyl methylcellulose, a binder in the amount of about 2% to about 7% by weight of the total composition.

Examples of lubricants suitable for use herein include sodium stearyl fumarate, magnesium stearate, zinc stearate, calcium stearate, talc, carnauba wax, stearic acid, palmitic acid, sodium stearyl fumarate, sodium laurel sulfate, glyceryl palmitostearate, palmitic acid, myristic acid and hydrogenated vegetable oils and fats. In certain embodiments of the present invention the composition includes sodium stearyl fumarate, a lubricant in the amount of about 1.25% to about 5% by weight of the total composition. In one of the particular embodiments, the composition of the present invention comprises sodium stearyl fumarate, a lubricant in the amount of about 1.5% by weight of the total composition.

Examples of glidants suitable for use herein include talc, colloidal silicon dioxide, silicic acid, cornstarch, calcium silicate, magnesium carbonate, magnesium oxide, magnesium silicate, starch, castor wax. In certain embodiments of the present invention the composition includes colloidal silicon dioxide, a glidant in the amount of about 0.5% to about 5% by weight of the total composition, in one of the particular embodiments, the composition of the present invention comprises colloidal silicon dioxide, a glidant in the amount of about 0.5% to about 2% by weight of the total composition.

In certain embodiments, the composition of the present invention includes tablets comprising eluxadoline and excipients selected from silicified microcrystalline cellulose, mannitol, hydroxypropyl methylcellulose, crospovidone, colloidal silicon dioxide, sodium stearyl fumarate and optionally, coating agents.

In one of the particular embodiments, the present invention provides a pharmaceutical composition comprising:
(a) Eluxadoline or a prodrug or a pharmaceutically acceptable thereof, in an amount from about 5 to 20% by weight of the total composition;
(b) Diluents selected from combination of silicified microcrystalline cellulose in an amount from about 60% to about 70% by weight of the total composition and mannitol in an amount from about 8% to about 12% by weight of the total composition
(c) Hypromellose in an amount from about 2% to about 7% by weight of the total composition;
(d) Crospovidone in an amount from 0% to about 2.5% by weight of the total composition;
(e) Colloidal silicon dioxide in an amount from about 0.5% to about 2% by weight of the total composition;
(f) Sodium stearyl fumarate in an amount of about 1.5% by weight of the total composition;
and
(g) Optionally coating agent(s).

The process of preparation of dosage forms in accordance with the embodiments depicted herein are manufactured by standard techniques. For example tablets are conventionally prepared by wet granulation, dry granulation and direct compression. Direct compression (DC) is the preferred and simplest process for the preparation of tablets. DC involves a single step process i.e. proper blend of active ingredient with appropriate excipients before compression. Apart from simplicity of formulation and manufacturing process, the key advantages of direct compression includes reduced capital, labour and energy costs for manufacturing and the avoidance of water/solvent during granulation for sensitive drug substances. In preferred embodiments, the present invention tablets can be prepared by direct compression. In a particular embodiment, for example the dosage form may be manufactured by the direct compression technique. In the direct compression technique, tablets are compressed directly from blends of active ingredients and excipients including diluent, disintegrant, lubricant and other additives. Direct compression process is preferred over other manufacturing process by considering hygroscopic nature of API, concentration of API and ease of manufacturing under controlled environmental condition (Temperature: NMT 27° C. and RH: NMT 30%).

In certain embodiments, the process of making an oral pharmaceutical composition comprising Eluxadoline or a pharmaceutically acceptable salt thereof or a prodrug thereof prepared by: i) blending eluxadoline or a pharmaceutically acceptable salt or a prodrug thereof, with the pharmaceutically acceptable inert excipients selected from one or more of: diluent(s), binder(s), disintegrant(s), glidant(s); ii) lubricating the above blend with the addition of lubricant(s); iii) compressing the dry blend into suitably sized tablets and optionally a film coating, or filling the dry blend into capsules.

In one of the particular embodiments, the process of making an oral pharmaceutical composition comprising: i) blending eluxadoline or a pharmaceutically acceptable salt or a prodrug thereof, with the pharmaceutically acceptable inert excipients: silicified microcrystalline cellulose, mannitol, hypromellose, colloidal silica and crospovidone; ii) lubricating the above blend with the addition of sodium stearyl fumarate; iii) compressing the dry blend into suitably sized tablets, or filling into capsules.

In certain embodiments, the process of making an oral pharmaceutical composition comprising Eluxadoline or a pharmaceutically acceptable salt thereof or a prodrug thereof prepared by
Step-I: Blending eluxadoline or a pharmaceutically acceptable salt or a prodrug thereof, with 50% diluent(s) & glidant(s);
Step-II: materials of step I were co-milled with finer size mesh at desired speed.
Step-III: sifted material of step II was mixed with remaining 50% diluent(s), disintegrant(s) binder(s), and then co-shifted & blended for 10 minutes.
Step-IV: lubricant(s) was shifted separately and material of step III was lubricated with lubricant(s) and blend for 5 minutes.
Step-V: lubricated blend of step IV was compressed in to suitably sized tablets, or filling into capsules.

In one of the particular embodiments, the process of making an oral pharmaceutical composition comprising Eluxadoline or a pharmaceutically acceptable salt thereof or a prodrug thereof prepared by:
Step-I: Blending eluxadoline or a pharmaceutically acceptable salt or a prodrug thereof, with 50% silicified microcrystalline cellulose, mannitol, colloidal silica
Step-II: materials of step I were co-milled with finer size mesh at desired speed.
Step-III: sifted material of step II was mixed with remaining 50% of silicified microcrystalline cellulose, hypromellose, crospovidone and then co-shifted & blended for 10 minutes.
Step-IV: sodium stearyl fumarate was shifted separately and material of step III was lubricated with sodium stearyl fumarate and blend for 5 Minutes.
Step V: lubricated blend of step IV was compressed in to suitably sized tablets, or filling into capsules In certain embodiments, the tablets of the invention has an optional protective outer layer i.e. tablet coating. The protective outer layer of the tablet is based on the weight of the pharmaceutical composition. The composition can contain at least one coating layer polymer and a coating solvent, for example, water, which is used for processing and removed by drying. Suitable examples of polymer for the coating layer include, but are not limited to, hydroxypropyl methylcellulose, polyvinyl alcohol (PVA), ethyl cellulose, methacrylic polymers, hydroxypropyl cellulose, and starch. In one of the particular embodiments, the coating layer polymer is polyvinyl alcohol (PVA).

In one of the particular embodiments of the present invention the film coat composition comprises plasticizer. Suitable plasticizers include, but are not limited to, glycerol monocaprylocaprate, triacetin, diethyl phthalate, tributyl sebacate, polyethylene glycol (PEG), glycerin, and triethyl citrate. In one of the particular embodiments, the plasticizer is glycerol monocaprylocaprate.

In certain embodiments, the film coat composition may optionally comprises an anti-adherent or glidant. Suitable anti-adherent or glidant include, but are not limited to, such as talc, fumed silica, or magnesium stearate. In one of the particular embodiments, the coating layer contains talc.

In certain embodiments, the film coat composition may optionally comprises a surfactant such as sodium lauryl sulfate and polysorbate 80. In one of the particular embodiments, the surfactant is sodium lauryl sulfate.

In certain embodiments, the film coating composition may optionally comprises an opacifying agent or dyes, such as aluminum lakes, iron oxides, titanium dioxide and natural colors. In preferred embodiment, the opacifying agent is titanium dioxide.

In one of the particular embodiments, the film coating composition comprising polyvinyl alcohol (PVA), talc, titanium dioxide, glycerol monocaprylocaprate type-1, sodium lauryl sulphate, iron oxide yellow, iron oxide red.

In one of the particular embodiments, the film coating composition may function as High performance moisture barrier film-coating. Usually such moisture barrier film-coating compositions are conventionally known in the art. For example, in one of the particular embodiments, the film coating composition is Opadry AMB II (pink/beige) in an amount of from about 0% to about 10% by weight of the tablet; preferrably, in an amount of from about 0% to about 6% by weight of the tablet; and more preferrably in an amount of from about 0% to about 3% by weight of the tablet.

In certain embodiments, the present invention relates to oral pharmaceutical compositions comprising an opioid receptor modulator, process for the preparation thereof and administration of such compositions for opioid receptor related disorders including, for example, pain and gastrointestinal disorders such as diarrheic syndromes, motility disorders including post-operative ileus and constipation, and visceral pain including post-operative pain, irritable bowel syndrome and inflammatory bowel disorders.

In certain embodiments, the present invention provides an oral pharmaceutical compositions comprising eluxadoline or a pharmaceutically acceptable salt thereof or a prodrug thereof, process for the preparation thereof and administration of such compositions for irritable bowel syndrome (IBS-D).

The following examples are intended to serve as illustrations of the present invention only and do not restrict the scope of the invention in any manner whatsoever.

EXAMPLES

Example 1

| Sr. No | Ingredients | Quantity/Tablet (mg) | % w/w (mg) |
|---|---|---|---|
| I. Core Tablets | | | |
| Ia) Pre-lubrication | | | |
| 1 | Eluxadoline | 100.00 | 12.50 |
| 2 | Silicified Microcrystalline Cellulose USNF | 512.00 | 64.00 |
| 3 | Mannitol USP | 96.00 | 12.00 |
| 4 | Colloidal silicon dioxide USNF | 12.00 | 1.50 |
| 5 | Crospovidone USNF | 20.00 | 2.50 |
| 6 | Hypromellose USP | 48.00 | 6.00 |
| Ib) Lubrication | | | |
| 7 | Sodium Stearyl Fumarate USNF | 12.00 | 1.50 |
| | Core Table Weight (mg) | 800.00 | 100.00 |
| II. Film-Coating | | | |
| 8 | Opadry ® AMB II | 31.20 | 3.90 |
| 9 | Purified water USP♦ | q.s | q.s |

♦Processing solvent. Not present in the final product, except traces.
Opadry ® AMB II contains: Polyvinyl alcohol, Titanium dioxide and Talc, glycerol Monocaprylocaprate type-1, sodium lauryl sulphate, iron oxide yellow, iron oxide red.

Manufacturing Procedure:
Core Tablet:
  Step 1: Eluxadoline, colloidal silicon dioxide, mannitol and 50% w/w silicified microcrystalline cellulose were co-sifted.
  Step 2: Materials of step 1 were milled with finer size mesh at desired speed.
  Step 3: Sifted material of step 2 was mixed with remaining 50% w/w silicified microcrystalline cellulose, hypromellose and crospovidone and then co-sifted.
  Step 4: Sodium stearyl fumarate was sifted separately.
Blending and Lubrication:
  Step 5: Material of step 3 was loaded into suitable blender and then blended for 10 minutes.
  Step 6: Material of step 5 was lubricated with step 4 material and then blended for 5 minutes.
Compression:
  Step 7: Lubricated blend of step 6 was compressed into tablets.
Coating:
  Step 8: Opadry was dispersed into purified water with continuous stirring.
  Step 9: The core tablets of step 7 were coated with aqueous dispersion of Opadry for desired weight gain.

Example 2

| Sr. No | Ingredients | Quantity/Tablet (mg) | % w/w (mg) |
|---|---|---|---|
| I. Core Tablets | | | |
| Ia) Pre-lubrication | | | |
| 1 | Eluxadoline | 100.00 | 12.50 |
| 2 | Silicified Microcrystalline Cellulose USNF | 572.00 | 71.50 |
| 3 | Mannitol USP | 80.00 | 10.00 |
| 4 | Colloidal silicon dioxide USNF | 6.00 | 0.75 |
| 5 | Crospovidone USNF | 10.00 | 1.25 |
| 6 | Hypromellose USP | 20.00 | 2.50 |
| Ib) Lubrication | | | |
| 7 | Sodium Stearyl Fumarate USNF | 12.00 | 1.50 |
| | Core Tablet Weight (mg) | 800.00 | 100.00 |
| II. Film-Coating | | | |
| 8 | Opadry ® AMB II | 31.20 | 3.90 |
| 9 | Purified water USP♦ | q.s | q.s |

♦Processing solvent. Not present in the final product, except traces.
Opadry ® AMB II contains: Polyvinyl alcohol, Titanium dioxide and Talc, glycerol Monocaprylocaprate type-1, sodium lauryl sulphate, iron oxide yellow, iron oxide red.

Manufacturing Procedure:
Core Tablet:
  Step 1: Eluxadoline, colloidal silicon dioxide, mannitol and 50% w/w silicified microcrystalline cellulose were co-sifted.
  Step 2: Materials of step 1 were milled with finer size mesh at desired speed.
  Step 3: Sifted material of step 2 was mixed with remaining 50% w/w silicified microcrystalline cellulose, hypromellose and crospovidone and then co-sifted.
  Step 4: Sodium stearyl fumarate was sifted separately.
Blending and Lubrication:
  Step 5: Material of step 3 was loaded into suitable blender and then blended for 10 minutes.
  Step 6: Material of step 5 was lubricated with step 4 material and then blended for 5 minutes.

Compression:
  Step 7: Lubricated blend of step 6 was compressed into tablets.
Coating:
  Step 8: Opadry was dispersed into purified water with continuous stirring.
  Step 9: The core tablets of step 7 were coated with aqueous dispersion of Opadry for desired weight gain Example 3

| Sr. No | Ingredients | Quantity/Tablet (mg) | % w/w (mg) |
|---|---|---|---|
| | I. Core Tablets | | |
| | Ia) Pre-lubrication | | |
| 1 | Eluxadoline | 100.00 | 12.50 |
| 2 | Silicified Microcrystalline Cellulose | 560.00 | 70.00 |
| 3 | Mannitol | 96.00 | 12.00 |
| 4 | Colloidal silicon dioxide | 12.00 | 1.50 |
| 5 | Hypromellose | 20.00 | 2.50 |
| | Ib) Lubrication | | |
| 6 | Sodium Stearyl Fumarate | 12.00 | 1.50 |
| Core | Tablet Weight (mg) | 800.00 | 100.00 |
| | II. Film-Coating | | |
| 7 | Opadry ® AMB II | 31.20 | 3.90 |
| 8 | Purified water | q.s | q.s |

*: Processing solvent. Not present in the final product, except traces.
Opadry ® AMB II contains: Polyvinyl alcohol, Titanium dioxide and Talc, glycerol Monocaprylocaprate type-1, sodium lauryl sulphate, iron oxide yellow, iron oxide red.

Manufacturing Procedure:
Core Tablet:
  Step 1: Eluxadoline, colloidal silicon dioxide, mannitol and 50% w/w silicified microcrystalline cellulose were co-sifted.
  Step 2: Materials of step 1 were milled with finer size mesh at desired speed.
  Step 3: Sifted material of step 2 was mixed with remaining 50% w/w silicified microcrystalline cellulose and hypromellose and then co-sifted.
  Step 4: Sodium stearyl fumarate was sifted separately.
Blending and Lubrication:
  Step 5: Material of step 3 was loaded into suitable blender and then blended for 10 minutes.
  Step 6: Material of step 5 was lubricated with step 4 material and then blended for 5 minutes.
Compression:
  Step 7: Lubricated blend of step 6 was compressed into tablets.
Coating:
  Step 8: Opadry was dispersed into purified water with continuous stirring.
  Step 9: The core tablets of step 7 were coated with aqueous dispersion of Opadry for desired weight gain.

Example 4

| Sr. No | Ingredients | Quantity/Tablet (mg) | % w/w (mg) |
|---|---|---|---|
| | I. Core Tablets | | |
| | Ia) Pre-lubrication | | |
| 1 | Eluxadoline | 100.00 | 12.50 |
| 2 | Silicified Microcrystalline Cellulose | 512.00 | 64.00 |
| 3 | Lactose | 96.00 | 12.00 |
| 4 | Colloidal silicon dioxide | 12.00 | 1.50 |
| 5 | Crospovidone | 20.00 | 2.50 |
| 6 | Hypromellose | 48.00 | 6.00 |
| | Ib) Lubrication | | |
| 7 | Sodium Stearyl Fumarate | 12.00 | 1.50 |
| | Core Tablet Weight (mg) | 800.00 | 100.00 |
| | II. Film-Coating | | |
| 8 | Opadry ® AMB II | 31.20 | 3.90 |
| 9 | Purified water | q.s | q.s |

*: Processing solvent. Not present in the final product, except traces.
Opadry ® AMB II contains: Polyvinyl alcohol, Titanium dioxide and Talc, glycerol Monocaprylocaprate type-1, sodium lauryl sulphate, iron oxide yellow, iron oxide red.

Manufacturing Procedure:
Core Tablet:
  Step 1: Eluxadoline, colloidal silicon dioxide, lactose and 50% w/w silicified microcrystalline cellulose were co-sifted.
  Step 2: Materials of step 1 were milled with finer size mesh at desired speed.
  Step 3: Sifted material of step 2 was mixed with remaining 50% w/w silicified microcrystalline cellulose, hypromellose and crospovidone and then co-sifted through a suitable sieve and re-sift.
  Step 4: Sodium stearyl fumarate was sifted separately.
Blending and Lubrication:
  Step 5: Material of step 3 was loaded into suitable blender and then blended for 10 minutes.
  Step 6: Material of step 5 was lubricated with step 4 material and then blended for 5 minutes.
Compression:
  Step 7: Lubricated blend of step 6 was compressed into tablets.
Coating:
  Step 8: Opadry was dispersed into purified water with continuous stirring.
  Step 9: The core tablets of step 7 were coated with aqueous dispersion of Opadry for desired weight gain.

The dissolution profiles were determined for example 1 & example 2 Tablets and the results are shown in below table.

Dissolution Profile:
  Medium: 0.05M Phosphate buffer PH 4.5
  Method: Basket (USP Apparatus-I); 100 RPM
  Time intervals: 5, 10, 15, 20, 30, & 45 Minutes

| Time intervals | % Drug released | | |
|---|---|---|---|
| (Minutes) | Example-1 | Example-2 | Viberzi ® Tablets |
| 5 | 53 | Not determined | 65 |
| 10 | 68 | 90 | 83 |
| 15 | 80 | 99 | 92 |
| 20 | 89 | 101 | 95 |
| 30 | 95 | 103 | 97 |
| 45 | 100 | Not determined | 100 |

Extraction Study:
  The Extraction study data of eluxadoline tablets was determined for example 1 Tablets and the results are shown in below table.
  With water at 25° c. for 10 min, 1 hr and 12 hr:
    a) Tablet technique: One tablet (equivalent to 100 mg) was taken in to a beaker and 10 ml of water was added and kept on bench top at given time points.

b) Powder technique: Tablet powder equivalent to 100 mg was taken into a beaker and 10 ml of water was added and kept on bench top for at given time points.

With saline at 25° c. for 10 min, 1 hr and 12 hr:
a) Tablet technique: One tablet (equivalent to 100 mg) was taken to a beaker and 10 ml of water was added and kept on bench top at given time points.
b) Powder technique: Tablet powder equivalent to 100 mg was taken into a beaker and 10 ml of water was added and kept on bench top at given time points.

The samples were filtered by using (Whatman GF/C) at given time points (10 min, 1 hr and 12 hr. points). The final sample solutions were analysed for release in the extraction by adopting Assay method.

The concentration of eluxadoline in the extraction assessment are shown in below table.

Extraction study data of Eluxadoline Tablets 100 mg

Example-1
Extraction Temperature (° C.)
25° C.
Extraction Media

| Time | Water | | Saline | |
| --- | --- | --- | --- | --- |
| | Tablet | Powder | Tablet | Powder |
| | mg/mL of Eluxadoline | | | |
| 10 min | 0.135 | 0.051 | 0.126 | 0.117 |
| 1 hr. | 0.199 | 0.129 | 0.180 | 0.237 |
| 12 hr. | 0.222 | 0.287 | 0.194 | 0.293 |

We claim:

1. A pharmaceutical tablet composition comprising:
(a) Eluxadoline in an amount from 5 to 20% by weight of the total composition;
(b) diluents selected from combination of silicified microcrystalline cellulose in an amount from 60% to 70% by weight of the total composition and mannitol in an amount from 8% to 12% by weight of the total composition;
(c) hypromellose in an amount from 2% to 7% by weight of the total composition;
(d) crospovidone in an amount from 0% to 2.5% by weight of the total composition;
(e) colloidal silicon dioxide in an amount from 0.5% to 2% by weight of the total Composition;
(f) sodium stearyl fumarate in an amount from 1.5% to 3% by weight of the total Composition;
(g) optionally coating agent;
wherein extraction of the tablet composition with water or saline at 25° C. for up to 12 hours produces a concentration of eluxadoline of less than or approximately 1 mg/ml.

2. A process of making a pharmaceutical tablet composition, wherein the tablet composition is made by the following steps:
Step-I: blending eluxadoline with part of silicified microcrystalline cellulose, mannitol, colloidal silicon dioxide;
Step-II: co-milling materials of step I;
Step-III: sifting material of step II and mixing with remaining part of silicified microcrystalline cellulose, hypromellose, crospovidone and then co-sifting & blending;
Step-IV: sifting sodium stearyl fumarate separately and lubricating the material of step III with sodium stearyl fumarate into a blend;
Step V: compressing the blend of step IV in to tablets.

3. The pharmaceutical tablet composition according to claim 1, wherein the tablet releases at least 80% of the eluxadoline within 15 minutes in 0.05M phosphate buffer, pH 4.5, 900 ml, 100 RPM, accordance with USP <711> Type-I basket apparatus.

4. The pharmaceutical tablet composition according to claim 1, wherein said tablet composition is useful for effective treatment of opioid receptor disorder while minimizing or elimination of potential abuse or diversion of such composition.

* * * * *